United States Patent [19]

Brody

[11] Patent Number: 5,058,602

[45] Date of Patent: Oct. 22, 1991

[54] PARASPINAL ELECTROMYOGRAPHY SCANNING

[76] Inventor: Stanley R. Brody, R.F.D. #1, Wurtsboro, N.Y. 12790

[21] Appl. No.: 418,751

[22] Filed: Oct. 4, 1989

Related U.S. Application Data

[63] Continuation-in-part of Ser. No. 252,270, Sep. 30, 1988, abandoned.

[51] Int. Cl.$^5$ ............................................. A61B 5/0488
[52] U.S. Cl. ..................................... 128/733; 128/734
[58] Field of Search ................. 128/733, 774, 781, 782

[56] References Cited

U.S. PATENT DOCUMENTS

| | | | |
|---|---|---|---|
| 4,664,130 | 5/1987 | Gracovetsky | 128/733 |
| 4,667,513 | 5/1987 | Konno | 128/733 |
| 4,807,642 | 2/1989 | Brown | 128/733 |
| 4,971,069 | 11/1990 | Gracovetsky | 128/733 |

OTHER PUBLICATIONS

EMG Systems by Hartfield; *Digest of Chiropractic Economics*, Sep.–Oct., 1987.
Hartfield 301 EMG Scanner.
Hartfield 501 EMG Scanner.
Kent et al., "Potential Applications for EMG in Chiropractic Practice", *Digest of Chiropractic Economics*, Sep.–Oct., 1987.
Brody, "Practical Chiropractic EMG", *The Digest of Chiropractic Economics*, Sep.–Oct., 1987.

*Primary Examiner*—Lee S. Cohen
*Assistant Examiner*—Krista M. Pfaffle
*Attorney, Agent, or Firm*—Weingram & Zall

[57] ABSTRACT

A method of electromyographic scanning paravertebral muscles comprising measuring electrical potential across a persons's spinous process bilaterally across segments of the spinous process.

15 Claims, No Drawings

PARASPINAL ELECTROMYOGRAPHY SCANNING

RELATED APPLICATIONS

This application is a continuation-in-part, of U.S. Ser. No. 07/252,270, filed Sept. 30, 1988 now abandoned. The entire disclosure of this application is incorporated herein by reference.

BACKGROUND OF THE INVENTION

The continuous concerns of chiropractors have been:
1. Whether, when and how to adjust patients;
2. How to quantify and objectively document palpatory findings of muscle tension and related soft tissue changes;
3. How to improve results by developing methods where patient care continues outside the office, and corrective changes occur between visits;
4. How to monitor dynamic changes in nervous system function during a course of chiropractic care;
5. How to determine which adjunctive procedures are helpful in a given case;

Development of alternatives to radiography for postural analysis in scoliosis screening and lift therapy; and 7. Development of instrumentation and protocols which can be used to demonstrate soft tissue involvement to third parties, including attorneys and insurance companies.

It is well-known, that the electrical potentials associated with muscular activity may be measured and recorded. This technique is known as electromyography ("EMG"). The use of electromyography in patients suffering from low back pain is commonly accepted in the medical community. The osteopathic profession has used electromyography to verify the presence of palpable lesion of the spine.

Generally, EMG electrodes are placed on the surface of the skin overlying the muscles being evaluated, or needle electrodes are employed which penetrate the tissue being studied. In addition to the active electrodes, a ground reference electrode is also applied to the patient. The signal from these electrodes is very feeble and is typically measured in microvolts. A preamplifier, followed by one or more additional stages of amplification boosts the signal to a usable level. Filters minimize the effects of interference arising from sources other than the muscles being studied. The amplified and filtered signal can be measured and/or displayed on a cathode ray tube. In addition, some machines are equipped with recorders which store the information on paper or magnetic media. Older vacuum tube equipment has largely been replaced by solid state apparatus.

Unfortunately, traditional electromyographic instrumentation has problems which limit its practical application in a chiropractic office, in that the equipment is often bulky and expensive and prone to instability and/or interferences; electrode application is complex and time-consuming; interpretation requires a high level of skill gained through extensive experience; and no protocols exist which are specifically designed for chiropractic practice.

Millions of Americans are incapacitated by chronic low back pain, and it is estimated that 80% of the general population will suffer from low back pain some time during their lives. The annual incidence of low back pain among workers has been reported to be 50 per 1,000. Despite the high incidence of low back pain, some clinicians have described 20–85% of all cases as having no definite discernible physical basis. The same is true with respect to cervical spine soft tissue injuries.

Most orthopedic examination procedures involve a physical maneuver designed to elicit pain or reduplicate symptoms. The inherent flaw in such techniques is subjectivity. The Examiner is dependent upon patient response in determining whether a given test is positive or negative. Neurological examination procedures suffer similar shortcomings. Sensory dermatome exams are dependent upon patient response. Manual muscle tests and deep tendon reflexes are dependent upon Examiner interpretation.

Soft tissue injuries often present ambiguous diagnostic findings. Complaints of pain may be accompanied by apparently normal radiographs. Symptoms are often intermittent. Orthopedic and neurological exam findings may be of questionable value because of Examiner bias and the desire of the patient to "prove" that the injury is "real." Thus, low back and cervical spine soft tissue claims are particularly difficult to evaluate. The independent Examiner needs hard data to substantiate claims of injury or malingering.

Electromyographic changes have been demonstrated in low back pain syndromes arising from a wide variety of etiologies. In some cases, abnormal electromyographic findings were present when other diagnostic tests were negative.

Surface electrode electromyography has been successfully employed by a number of investigators assessing low back pain. It has been demonstrated that muscular pain is associated with increased EMG activity. According to Dolce, et al, Psychol. Bull. 97, 3:502–520, 1985 ". . . the relation between painful and tender muscles and electromyographic activity are equivocal." They further state that "The most prevalent etiological hypothesis for myogenic back pain over the years has been that patients suffer due to increased muscle tension or spasm, although a model emphasizing low or asymmetric muscle activity has also been postulated."

Muscle tension backaches are frequently seen in chiropractic practice. It has been proposed that the muscular hyperactivity associated with back pain is due to a "vicious cycle" of pain producing tension and tension producing pain. This process is thought to be part of a protective mechanism for lesions of the spinal column. It is believed that increased involuntary muscle activity is an etiologic factor in chronic pain. In addition, it has been suggested that splinting and tensing of muscles leads to decreased blood flow, causing ischemic pain. Investigators have also discovered that back pain subjects demonstrate a generalized and sustained increase in skeletal muscle activity. Muscle spasm, therefore, is thought to be the "common denominator" in a variety of myogenic pain syndromes including fibrositis, interstitial myofibrositis, myogelosis, muscular rheumatism, nonarticular rheumatism, myofascial pain syndrome, myofascitis, myalgia, and trigger point pain.

Other investigators have described another mechanism to explain the muscular hyperactivity associated with spinal lesions. Facilitation of the anterior horn cells of the spinal cord has been demonstrated in "lesioned" segments. These cells are associated with efferent motor signals to skeletal muscle. The resulting lower thresholds, and hence increased impulse traffic, cause hypertonicity.

Clinical manifestations of vertebral subluxations often include hypertonicity, hyperalgesia, and decreased mobility. Research by Denslow, et al. JAOA 41:175, 1941 demonstrated that palpable spinal "lesions" correlated well with altered electromyographic activity. Electromyography may, therefore, be useful in quantifying aberrant muscular activity with could formerly be detected solely by palpation.

In addition to backache associated with local myospasm, abnormal electromyographic patterns have been demonstrated in patients with radicular symptoms. Khatri, et al., Arch. Neural., 41:594–497, 1984, used needle electromyography and computer tomography to examine 80 patients with low back pain accompanied by radiation down one or both extremities. The radiculapathies were due to disc involvement, canal stenosis, neural foramen narrowing, or facet joint degeneration. Khatri, et al., concluded: "The CT and EMG often agree. However, an abnormal EMG seems to correlate better with the demonstrated course of radiculopathy than CT."

Metastatic spinal or paraspinal disease may demonstrate abnormal electromyographic patterns. Boruta, et al. reported 54 cases with suspicious electromyograms who had known carcinoma at the time of admission. Boruta, et al. concluded: "Electromyography has been observed as a valuable adjunct in demonstrated paraspinous muscle metastasis in patients presenting with lumbosacral pain who had a known antecedent primary malignancy." In 16 additional cases without an antecedent history of malignancy, abnormal electromyographic findings were noted. In all 16 cases, a previously unsuspected metastatic malignancy was identified.

In addition to these conditions, electromyography has been used to evaluate manifestations of lumbar spinal canal stenosis, lumbar disc herniation, facet involvement, and abomalies of L-5. The effect of surgery, including laminectomy and surgery for nerve root compression have been studied using electromyography. Pfeiffer Acta. Univ. Carolina (Med.) suppl. 21:37–38, 1965, used electromyography to evaluate disturbances in spinal statics and dynamics in workers subjected to overstrain.

In the chiropractic profession, electromyography has been used primarily as a research tool. Electromyography has not been used extensively in the clinical practice of chiropractics. This may be due to a number of factors, including the cost and complexity of the apparatus, the time required to perform the examination, and a general lack of understanding of how electromyographic data may be useful to the chiropractic practioner.

Kent, et al., Digest of Chiro. Econ. 21, 4:30–33, 1979, used electromyography to evaluate a "vertebral challenge" technique of spinal analysis. Surface electrodes were applied to the paravertebral region. A two channel Meditron electromyograph was used, permitting the simultaneous display of potentials on each side of the spinal column.

Triano. JMPT 6, 1:13–16, Mar. 1983, employed electromyography as evidence for use of lift therapy. Thirty nine subjects with low back pain were examined using postural electromyography to assess their responses to heel lifts and ischial supports. He concluded that electromyography provided a greater degree of accuracy in lift placement than traditional radiographic methods.

Meeker. et al., JMPT 9, 4:257–266, Dec. 1986, published a review and summary of current research in neuromusculoskeletal thermography. The technique was compared with electromyography in addition to myelography, computed tomography and clinical and surgical findings. Spector, et al., JMPTs, 2:55–61, June, 1982, described a video integrated measurement system employing a number of non-invasive diagnostic modalities including electromyography, infrared thermography, posturometry, and moire contourography. Emphasis was placed upon the use of this system in biofeedback training.

After using several commercial electromyographic instruments, the inventor became involved in the development of equipment that could be used efficiently and accurately in the chiropractic office. The Hartfield 301 EMG scanner was the result of this effort (Hartfield Instruments Co., Wurtsboro, N.Y.). This instrument eliminates many of the shortcomings of earlier equipment.

This hand-held instrument permits rapid measurement of EMG potentials. The electrodes, preamplifier, readout, and related circuitry are contained in one compact unit. No complex electrode/cable sets need to be applied. The electrodes are "surface" electrodes, i.e., they are simply held against the site to be examiner.

The hand-held unit is equipped with silver-silver chloride post electrodes 2.5 cm apart. A ground reference electrode is placed on the wrist of the patient being examined. The electrodes are directly connected to a high impedance preamplifier. By placing the preamplifier at the electrode site, artifacts associated with environmental sources of electrical signals can be minimized.

A display is built into the hand-held unit, providing a digital readout of electromyographic potentials in microvolts. The instrument provides a bandwidth of 100 Hz to 200 Hz. If desired, signals may be fed from a hand-held electrode/preamplifier unit to a microcomputer to record and analyze the signals.

Biederman, Biofeedback and Self-Regulation, 9, 4:451–485, 1984, questioned the reliability of surface electrode electromyography in evaluating low back pain patients. Alleged sources of error cited were movement of the body, electrode placement, and electronic equipment instability. The equipment and protocols used by Biederman, however, are very different from those employed by the inventors. Cram performed a test-retest reliability study using this instrumentation. It was found that measurements of the trapesius were highly unstable, cephalic muscles showed good stability, and the paraspinal musculature in the lumbar region was highly stable.

SUMMARY OF THE INVENTION

A method of electromyographic scanning paravertebral muscles comprising measuring electrical potential bilaterally across segments of a persons spinous process.

A method of determining paravertebral muscular hyperactivity in a person comprising measuring electrical potential bilaterally across segments of the persons spinous process to obtain electrical potential measurements and comparing these measurements to a predetermined scale of electrical potential measurements.

Preferred electrodes are surface electrodes.

DETAILED DESCRIPTION OF THE INVENTION

Applicant has developed a protocol, i.e., method, for scanning the paravertebral muscles of the thoracic and lumbar spine. Although the method described herein is used on the lumbo-thoracic area, it may also be used in the cervical area.

The patient, in a prone position, rests for approximately five minutes. A ground electrode is fastened to the patient's wrist. The skin of the paravertebral region is cleansed with alcohol. Surface electrodes are placed so that the medial post is approximately 2.5 cm from the spinous process. Since the post spacing in the aforedescribed Hartfield 301 EMG Scanner is 2.5 cm., the lateral post is located approximately 5.0 cm from the spinous process.

The digital readout provides a true time integration that updates each 1.5 seconds. Generally, three seconds is the maximum time required to obtain a stable reading at a new site. In rare cases, the reading may fail to stabilize. In such cases a mid-value reading is recorded, and the instability noted in the record. Readings are taken bilaterally at the first sacral level, the fifth lumbar, and every other segment progressing caphaled and ending at the first thoracic segment.

Using this protocol and the hand-held scanner, a skilled clinician can complete an examination in less than five minutes, excluding acclimation time. The use of this procedure makes in-office diagnostic electromyography practical and cost effective. The inventor herein has used this procedure to document and quantify paravertebral muscle involvement, and to evaluate the effectiveness of chiropractic procedures on an individual basis.

There are, generally, two types of EMG electrodes:
1) inserted electrodes; and
2) surface electrodes.

Inserted electrodes include needle and wire electrodes inserted directly into the muscle being examined. They are useful in evaluating the function of a specific muscle, and the nerve supply to that specific muscle, for example, they may be used to evaluate medial nerve involvement in carpal tunnel syndrome.

Surface electrodes are useful in kinesiological studies. Such electrodes are applied to the skin overlying the muscles being evaluated. They may be used to evaluate the "global" function of groups of muscles.

Because of the anatomical and functional complexity of paraspinal muscles, it is preferred to use surface electrodes in order to determine functional changes in the paraspinal muscles.

The following table summarizes the characteristics of each type of electrode:

| INSERTED ELECTRODES | SURFACE ELECTRODES |
| --- | --- |
| More specific; useful in studying single muscles. | record composite potentials of muscles working together; useful in studying groups of muscles working together. |
| Invasive; may cause infection, nerve injury, et. | Non-invasive; painless. |
| Difficult to duplicate exact insertion point and depth. | East to duplicate protocols for longitudinal studies. |
| Better resolution of high frequencies. | Some high frequency loss (of little concern of chiropractic work). |
| Act of insertion may elicit "insertion potentials" | No insertion potential artifacts. |
| Inferior test-retest reliability | Very good test-retest reliability. |

Komi, et al., Electromyography 10:357–367, 1970, investigated the test-retest reliability of surface vs. wire electrodes. The average test retest reliability for surface electrodes was 0.88, compared to 0.62 for inserted electrodes. The day to day reliability of surface electrodes was also found superior to that of inserted electrodes. It has been reported that the mean reliability coefficient for surface electrode EMG readings is 0.83.

Thus, the needle technique is very selective, and may be used to measure the activity of a single muscle. Needles provide better high frequency resolution, which may be useful in the diagnosis of some muscle diseases. Unfortunately, their test-retest reliability is inferior to that of surface electrodes. Therefore, they are not well suited to measuring changes in global function of groups of muscles. Needle insertion may result in pain, nerve damage, or infection.

Surface electrode techniques are painless, non-invasive, and useful in recording the functional activity of groups of muscles working together. In addition, such readings exhibit very good reliability, and may be used to monitor patient progress during a course of professional care. Although both needle and surface electrode techniques are accepted diagnostic and research tools, surface electrodes are more appropriate for recording paraspinal potentials in chiropractic practice.

Paraspinal EMG scans can be rapidly interpreted. To assist the doctor, a rough scale to apply to the case presentations follows:

(a) 0.3–0.5 uv indicates the muscles are in a resting state of tonus, and not actively contracting.
(b) 0.6–0.7 uv indicates some random firing above the base line just described. These may develop into problem areas.
(c) 0.8–1.1 uv are problem areas exhibiting palpable spasticity and tenderness.
(d) 1.2 uv or greater readings are found in problem areas demonstrating pain and marked spasm.

This scale is applicable only to scans performed with the patient prone. Standing readings are considerably higher, and exhibit greater variability.

With the foregoing general technique, it is possible to develop information relating to the spinal condition heretofore unavailable.

For example, a six-point orthopedic range of motion ("ROM") exam has been developed to display the spine as it exists in a state of motion. The exam consists of developing EMG patterns, using the method of this invention, for:

(a) neutral standing
(b) flexion
(c) left and right lateral flexion
(d) left and right rotation Using a computer to assist the EMG scanning, it is possible to virtually see the dynamics of the spine as one would in a stop action motion picture.

After reviewing many range of motion EMGs, it is the opinion of the inventor that there are several basic paraspinal EMG patterns. While present definition of these patterns may become more refined in the future, the foregoing patterns are basic and should be viewed as working models for further refinement and expansion.

The Neutral Pattern

A person standing in a relaxed neutral anatomical position should have a level pelvis and a vertical spine with muscles balanced on each side of the spine at each vertebral level.

For example, the classic EMG pattern for the neutral position is as follows:

|    | L* | R* | Difference |   |
|----|----|----|------------|---|
|    |    |    | L          | R |
| T1 | 35 | 35 | —          |   |
| T3 | 33 | 33 | —          |   |
| T5 | 29 | 29 | —          |   |
| T7 | 28 | 28 | —          |   |
| T9 | 21 | 21 | —          |   |
| T11| 34 | 34 | —          |   |
| L1 | 24 | 24 | —          |   |
| L3 | 27 | 27 | —          |   |
| L5 | 31 | 31 | —          |   |
| S1 | 28 | 28 | —          |   |

*millivolts

Paravertebral EMG levels should range from 2.5 to 4.0 microvolts. The muscles are relatively relaxed, but are holding up the spine. The difference between the right and left readings equals zero. Of course, this is an ideal situation, and differences of up 20% should only be viewed as postural balancing and nothing more. Higher differences demonstrate a pathological tendency.

The Forward Flexion Pattern

The forward bending position should show basically the same view and may present slightly higher readings in the low back. They should not be markedly elevated, however. Readings exceeding 5.0 or 6.0 microvolts warrant further investigation.

The Right and Left Lateral Position

Lateral flexion requires an altogether different kind of action from the spine. In right flexion from a standing position, the right vertebral muscles start to contract causing the spine to move to the right side. Very little exertion is needed by these muscles to cause the body to yield to gravity. The muscles just need to cause the vertebral column to become concave on the side of flexion. It is the muscles on the opposite side of flexion which have to act as antigravity muscles to hold the body up and keep it from falling. Therefore, the classic EMG pattern in right lateral flexion is as follows:

|    | L* | R* | Difference |   |
|----|----|----|------------|---|
|    |    |    | L          | R |
| T1 | 72 | 45 | 27         |   |
| T3 | 54 | 31 | 23         |   |
| T5 | 62 | 35 | 27         |   |
| T7 | 59 | 27 | 32         |   |
| T9 | 73 | 41 | 32         |   |
| T11| 49 | 28 | 21         |   |
| L1 | 59 | 31 | 28         |   |
| L3 | 47 | 27 | 20         |   |
| L5 | 41 | 18 | 23         |   |
| S1 | 45 | 22 | 23         |   |

*millivolts

Notice that the left-sided muscles exhibit potentials that are almost twice as high as those on the right side. Right-sided potentials usually range from 2.0 and 4.0 microvolts. The left side typically exhibits potentials in the 4.0 to 7.0 microvolts range. Numbers that are exceptionally high or low warrant further investigation.

Left flexion, of course, will produce readings that are opposite right flexion.

Right and Left Rotation

Right rotation shows an altogether different pattern. Numbers are high in the left lower back until T-10. Then there is a crossover, with the right side becoming high until T-1. A classic EMG pattern for right rotation is as follows:

|    | L* | R* | Difference |    |
|----|----|----|------------|----|
|    |    |    | L          | R  |
| T1 | 21 | 45 |            | 24 |
| T3 | 18 | 42 |            | 34 |
| T5 | 21 | 35 |            | 14 |
| T7 | 14 | 21 |            | 7  |
| T9 | 12 | 17 |            | 5  |
| T11| 15 | 13 | 2          |    |
| L1 | 27 | 15 | 12         |    |
| L3 | 46 | 26 | 20         |    |
| L5 | 45 | 18 | 27         |    |
| S1 | 53 | 21 | 32         |    |

Very often the numbers will appear high at the top and bottom of the chart coming close to "0" difference at T-10 where the lowest fixed rib is located. Of course, left rotation will be opposite.

The foregoing provides generalizations about EMG scans, using the method of this invention for range of motion ("ROM") exams. A case study is provided in Example 20.

Through the aid of a computer system, it is relatively easy to develop indices, graphs, and readings to assist the chiropractor in diagnosis and treatment. For example, the following have been developed:

COMFORT INDEX

The comfort index is the average of muscular activity on one side of the body. It is expressed as "comfort index right" or "comfort index left". The comfort index is measured in microvolts. Their rating value is as follows:

| .1–3.9   | muscular positioning |
| 4.0–5.9  | tense muscles        |
| 6.0–6.9  | light pain           |
| 7.0–10.0 | moderate pain        |
| 10.1–up  | acute pain           |

While the comfort index can indicate the general nature of spinal spasticity, it cannot indicate specific vertebral level myospasm.

BALANCE INDEX

Balance index is the ratio of the sum of muscular activity on the right side of the spine vs. muscular activity on the left side of the spine. An imbalance indicates that the patient is leaning towards the side of lesser activity.

SCOLIOSIS INDEX

The scoliosis index indicates the side of the body that contains the highest amount of vertebral segments that have rotated away from the center line of the spine.

MUSCULAR SPASM INDEX

The muscular spasm file displays any segment with a raw data value of 7.0 microvolts or more, as "SPASM" and a raw data value of 1.4 microvolts or less, as "HYPO". Hypo function is the inability of the muscle to produce enough contraction to properly control the anatomical positioning of the segment.

HYPO FUNCTION INDEX

The hypo function index measures the side of the body that contains the highest amount of hypo function.

MUSCULAR BALANCE INDEX

The muscular imbalance index is a combination of the muscular spasm index and the hypo function index. Its purpose is to give a total picture of the imbalance in the spine. Combining the left and right readings will give an accurate picture of which ranges of motion are most stable or unstable.

RANGE OF MOTION INDEX

The range of motion index is the right and left side of the "muscular balance index," combined to act as a guide to understand which range of motion is the most imbalanced. Putting the ROM INDEX in ascending or descending order will accomplish this. The doctor can then use appropriate exercises or therapeutic maneuvers.

PERCENT DIFFERENCE FILE

The % difference file shows the percentage difference in muscular activity between the muscles on the left and the muscles on the right of each vertebral segment scanned.

ENHANCED DIFFERENCE FILE

The enhanced difference file displays a relative difference between the muscular activity on both sides by multiplying the "% difference" by the higher of the two values of the raw data for any given segment. This file shows a more accurate relationship when comparing all vertebral levels to each other.

SCOLIOSIS FILE

The scoliosis file displays any vertebral level that shows more than a 19% difference in vertebral rotation from the "% difference" file.

The scoliosis file display is "SCOL". More than a 19% difference is an indication of vertebral rotation and is not muscular positioning.

MUSCULAR SPASM FILE

The muscular imbalance file is a combination of the muscular spasm index and the hypo function index. Its purpose is to give a total picture of the imbalance in the spine. Combining the left and right readings will give an accurate picture of which ranges of motion are most stable or unstable.

SPINAL BALANCE CHART

The spinal balance chart displays in graphic form, the raw data in increments of 1.0 microvolts.

NERVE ROOT COMPRESSION FILE

The nerve root compression file shows the position of segment that move more than twice the distance than the segment above or below it. This indicates nerve root compression at the moment that the scan was performed. Nerve root compression may or may not show up clinically.

Chiropractors have relied heavily upon palpation of paraspinal muscles to locate vertebral suluxations. Generations of fledgling chiropractors have been trained to search the patient's back for "taut and tender" muscle fibers.

This highly subjective process has significant shortcomings. It is dependent entirely upon the skill of the Examiner and the perception of tenderness by the patient. Findings may vary from doctor to doctor. Finally, these subjective indicators are difficult, if not impossible, to quantify.

Electromyographic scanning permits the doctor to determine areas of muscular hyperactivity (e.g., spasm, splinting) quickly and accurately. By measuring surface EMG potentials directly in microvolts, the severity of the spasm can be evaluated, and case progress followed throughout a course of chiropractic care.

The paraspinal surface electrode EMG scanning as described herein can be used for: documenting the vertebral subluxation complex; evaluating soft tissue injury; range of motion studies; identifying areas of spasm; and legal documentation of injury, as well as other uses.

The method of this invention, can, for example, without any x-ray exposure:

(a) show the doctor the levels of muscular hypertonicity;
(b) indicate the levels of nerve root compression;
(c) demonstrate spinal scoliosis;
(d) pinpoint areas of spinal instability;
(e) map spinal range of motion charts that show which motions cause the spine to have problems and which motions relieve them.
(f) confirm blocks of vertebrae that move in an aberrant fashion;
(g) support patient's complains of problem area;
(i) show how to apply TENS therapy which maintains the adjustment outside of the office;
(j) tell the physician how to apply shoe lifts to balance the pelvis and straighten the spine;
(k) indicate which position the patient should be sleeping in to relieve nerve root compression;
(l) prescribe pillow placement under spinal curves during sleep to reduce nerve root compression;
(m) validate orthopedic exams with reliable, repeatable digital data;
(n) indicate the need to cease or continue care;
(o) perform seven part orthopedic exam, spinal range of motion survey (neutral, extension, left and right flexion, left and right rotation and flexion); and
(p) show the doctor when his technique is effective and when to change.

Equipment that can be used is well-known in the art. A particularly preferred EMG scanner useful in the method of this invention is the Hartfield 301 EMG Scanner. The scanner uses silver/silver chloride electrodes, 2.5 cm apart, has a high impedance amplifier and a band width of 100 Hz to 200 Hz. The device has an LED display in microvolts and stabilizes, typically, in under 3 seconds and is powered by a 9-volt battery.

Computer systems may also be used to assist in recording and analyzing EMG data. A preferred system is the Hartfield 501 EMG Scanner and associated software.

EXAMPLES

EXAMPLES 1-16

A total of 16 patients were examined using the protocol previously described; 14 were male and two were female. Ages ranged from 20 to 59 years. Thirteen had previous chiropractic care, and three were new patients.

In examining the findings obtained, two distinct patterns became apparent:

1. Low amplitude, symmetrical signal patterns.

These patterns exhibited the following characteristics:
  (a) Amplitude not exceeding 1.5 microvolts at any segmental level.
  (b) a difference of less than twice the value of the lesser number when comparing one side to another at a given level.

2. High amplitude, asymmetrical signal patterns.

These patterns exhibited the following characteristics:
  (a) Amplitude exceeding 1.5 microvolts at one or more segmental levels.
  (b) A difference of greater than twice the value of the lesser number when comparing one side to another at a given level.

Of the 16 patients examined, nine had low amplitude, symmetrical patterns (LS) and seven had high amplitude, asymmetrical patterns (HA). All three patients with no previous chiropractic care had HA patterns. Of the 13 patients undergoing a course of chiropractic care, nine demonstrated LS patterns and four had HA patterns. Ten of the patients examined had a history of low back pain and were undergoing a course of chiropractic care. Of these, seven had LS readings, and three had HA readings.

The equipment and protocols employed were found to be convenient for use in a chiropractic practice. In the patients scanned, 70% of those with a history of low back pain who were undergoing a course of chiropractic care exhibited low amplitude, symmetrical readings. All three patients with a history of low back pain and no previous chiropractic are exhibited high amplitude, asymmetrical readings.

TABLE I is a summary of the clinical findings and TABLE II(a) and II(b) are examples of low amplitude symmetrical readings and high amplitude asymmetrical readings, respectively.

TABLE I
SUMMARY OF CLINICAL FINDINGS

| Patient number | Sex | Age | Under care (chiropractic) | Symptoms | Type of reading (see text) |
|---|---|---|---|---|---|
| 1 | M | 30 | no | low back pain | HA |
| 2 | M | 20 | no | low back pain | HA |
| 3 | F | 41 | yes | low back pain | LS |
| 4 | M | 43 | yes | cerival and low back pain | LS |
| 5 | M | 59 | yes | low back pain | HA |
| 6 | M | 35 | yes | low back pain | LS |
| 7 | M | 35 | yes | low back pain | HA |
| 8 | M | 40 | yes | headache | LS |
| 9 | M | 21 | yes | low back pain | HA |
| 10 | F | 40 | yes | none | HA |
| 11 | M | 35 | no | cervical and low back pain | HA |
| 12 | M | 40 | yes | low back pain | LS |
| 13 | M | 20 | yes | none | LS |
| 14 | M | 42 | yes | low back pain | LS |
| 15 | M | 44 | yes | low back pain | LS |
| 16 | M | 24 | yes | low back pain | LS |

TABLE II
EXAMPLES OF LS VS. HA READINGS

| Segment | Left | Right |
|---|---|---|
| Example of low amplitude, symmetrical reading (Case 13) | | |
| T-1 | 0.3 | 0.3 |
| T-3 | 0.4 | 0.4 |
| T-5 | 0.5 | 0.5 |
| T-7 | 0.5 | 0.5 |
| T-9 | 0.4 | 0.5 |
| T-11 | 0.3 | 0.5 |
| L-1 | 0.3 | 0.4 |
| L-3 | 0.3 | 0.5 |
| L-5 | 0.5 | 0.5 |
| S-1 | 1.0 | 0.8 |
| Example of high amplitude, asymmetrical reading (Case 5) | | |
| T-1 | 1.8 | 2.1 |
| T-3 | 1.2 | 1.3 |
| T-5 | 1.1 | 1.1 |
| T-7 | 1.2 | 2.5 |
| T-9 | 1.3 | 2.9 |
| T-11 | 1.3 | 2.5 |
| L-1 | 4.0 | 2.6 |
| L-3 | 9.3 | 3.3 |
| L-5 | 16.0 | 2.5 |
| S-1 | 10.5 | 1.6 |

EXAMPLE 17

A mother aged 35 and her two daughters, aged 14 and 17, presented at the office for injuries sustained in an automobile accident. The 17-year old was the driver. The remaining two patients were passengers in the car at the time of the accident.

Mrs. A, the mother, was in the back seat when the car was struck broadside. She reported being "thrown around" in the car, striking the door, front seat, and headrest. She complained of dizziness, neck pain, and shoulder pain. After on-site examination of paramedics, she was taken to the emergency room of a nearby hospital. Treatment consisted of a prescription for pain medication and a sling. The patient has complained of continuous pain since.

A paraspinal EMG scan was performed with the patient prone. Electrodes were applied lateral to each side of the spinous process at S-1, L-5 and every other cephalad segment up to T-1. The potentials indicated were recorded. The patient was adjusted and a post adjustment scan performed. The results are shown in Table III.

TABLE III

| | Pre | | Post | |
|---|---|---|---|---|
| | L | R | L | R |
| T-1 | 1.1 | 1.0 | 0.8 | 0.7 |
| T-3 | 1.3 | 1.1 | 0.9 | 0.9 |
| T-5 | 0.9 | 0.8 | 0.9 | 0.7 |
| T-7 | 0.7 | 0.5 | 0.6 | 0.5 |
| T-9 | 0.5 | 0.4 | 0.6 | 0.5 |
| T-11 | 0.5 | 0.4 | 0.6 | 0.7 |
| L-1 | 0.4 | 0.3 | 0.3 | 0.4 |
| L-3 | 0.4 | 0.4 | 0.4 | 0.4 |
| L-5 | 0.3 | 0.3 | 0.4 | 0.4 |
| S-1 | 0.3 | 0.3 | 0.3 | 0.3 |

Note that following the adjustment, the high (greater than 1.0 uv) readings at the T-1 and T-3 levels were reduced, and that the "spread" of readings taken post adjustment was less than the "spread" of the pre-adjustment readings.

Ms. R, the 17-year-old driver of the car, hit the driver's door very hard at the time of impact. Her seat belt caused bruises across her chest. She went to the hospital with her mother complaining of shoulder pain. The pain still persists, and she quit her job because of it. Her pre and post EMG scans are shown in Table IV.

TABLE IV

|  | Pre | | Post | |
|---|---|---|---|---|
|  | L | R | L | R |
| T-1 | 4.4 | 1.0 | 1.3 | 0.9 |
| T-3 | 1.0 | 0.8 | 0.9 | 0.7 |
| T-5 | 0.8 | 0.5 | 0.8 | 0.9 |
| T-7 | 0.6 | 0.6 | 0.6 | 0.6 |
| T-9 | 0.7 | 0.5 | 0.7 | 0.9 |
| T-11 | 0.4 | 0.6 | 0.6 | 0.5 |
| L-1 | 2.1 | 0.6 | 0.5 | 0.5 |
| L-3 | 0.6 | 0.5 | 0.4 | 0.4 |
| L-5 | 0.3 | 0.3 | 0.3 | 0.3 |
| S-1 | 0.4 | 0.3 | 0.3 | 0.3 |

The results shown are even more striking than the preceding case. Note the marked reduction in readings at T-1 and L-1, and the overall improvement in the symmetry of readings pre and post adjustment.

Ms. B, the 14-year-old passenger, was asleep at the time of impact. She woke up upon striking the driver's seat with her knee. Her seat belt was loose, and she was "thrown around" in the car. When she stopped moving, her head was under the rear seat, and she was lying across the transmission hump. She went to the hospital with a painful, swollen knee, and was treated with an ice pack. An ice bandage was applied, and she was discharged.

She presented at the office complaining of episodic knee pain and low back pain. Her pre and post adjustment EMG scans are shown in Table V. Note the elevated, asymmetrical readings at T-3 and L-1 preadjustment, and the reduction in readings post-adjustment.

TABLE IV

|  | Pre | | Post | |
|---|---|---|---|---|
|  | L | R | L | R |
| T-1 | 1.5 | 1.5 | 1.4 | 1.6 |
| T-3 | 1.3 | 2.9 | 1.2 | 1.7 |
| T-5 | 0.9 | 1.4 | 0.9 | 1.0 |
| T-7 | 0.7 | 0.9 | 0.7 | 0.7 |
| T-9 | 0.5 | 0.6 | 0.6 | 0.9 |
| T-11 | 0.5 | 0.7 | 0.6 | 0.5 |
| L-1 | 0.6 | 3.1 | 0.6 | 0.6 |
| L-3 | 0.5 | 0.5 | 0.4 | 0.4 |
| L-5 | 0.4 | 0.3 | 0.3 | 0.3 |
| S-1 | 0.4 | 0.4 | 0.3 | 0.3 |

EXAMPLE 18

RESPONSE TO ADJUNCTIVE THERAPIES

A 29-year-old male with acute low back pain presented. He was examined by lumbar EMG scan in the prone position. Transcutaneous electrical nerve stimulation (TENS) was applied to the L-5 paravertebral region for ten minutes. The patient was permitted to rest for ten minutes following TENS application, and a post EMG scan was performed. The results were as follows:

| Segment | Left | Right |
|---|---|---|
|  | Pre TENS | |
| L-1 | 0.7 | 0.5 |
| L-3 | 0.7 | 0.5 |
| L-5 | 1.4 | 0.6 |
| S-1 | 0.5 | 0.5 |
|  | Post TENS | |
| L-1 | 0.5 | 0.4 |
| L-3 | 0.5 | 0.4 |
| L-5 | 0.4 | 0.4 |
| S-1 | 0.5 | 0.4 |

Discussion

The marked decrease in amplitude at the site of pain (L-5) is obvious, as is the symmetry demonstrated in the post reading. There was also marked improvement in symptomatology. Since TENS provides analgesia, it appears that in this patient the pain-spasm-pain cycle described by other investigators was broken using this modality.

EXAMPLE 19

POSTURAL STUDIES

Paraspinal EMG scans taken with the patient standing exhibit much higher readings than those taken with the patient prone. This is due to loading of the muscles and the increased activity necessary to maintain erect posture. Standing EMG scans have been used to evaluate lift therapy and in scoliosis screening.

Triano published a paper (JMPT 6, 1:13–16, March 1983) describing a technique using electromyography to evaluate lift therapy. Thirty-nine patients were examined. He concluded that electromyography was more accurate than radiography in determining lift placement.

Paraspinal EMG scanning and radiography have been employed to determine lift placement. After determining pelvic unleveling radiographically, four standing EMG scans were performed:
1. With no lift.
2. With the lift indicated by x-ray.
3. With a lift one size thicker than indicated by x-ray.
4. With a lift one size thinner than indicated by x-ray.

Case Studies

A 31-year-old male presented complaining of low back pain. His x-ray revealed a 5mm actual deficiency. The results of his standing EMG scans are shown in Table VI.

TABLE VI

| | Without Lift | | | With 3 mm Lift | | | With 5 mm Lift | | | With 6 mm Lift | |
|---|---|---|---|---|---|---|---|---|---|---|---|
| | L | R | | L | R | | L | R | | L | R |
| T-1 | 0.6 | 1.3 | T-1 | 0.9 | 0.8 | T-1 | 0.6 | 0.7 | T-1 | 0.6 | 0.5 |
| T-3 | 0.9 | 0.8 | T-3 | 1.0 | 1.0 | T-3 | 1.0 | 1.0 | T-3 | 0.9 | 0.9 |
| T-5 | 0.9 | 0.8 | T-5 | 1.1 | 0.8 | T-5 | 1.0 | 0.7 | T-5 | 0.9 | 0.6 |
| T-7 | 0.9 | 1.2 | T-7 | 1.0 | 1.0 | T-7 | 0.7 | 0.6 | T-7 | 0.9 | 0.8 |
| T-9 | 0.6 | 0.7 | T-0 | 1.0 | 1.0 | T-0 | 0.8 | 0.8 | T-9 | 0.9 | 0.9 |
| T-11 | 1.6 | 3.5 | T-11 | 1.9 | 3.0 | T-11 | 1.3 | 2.2 | T-11 | 0.8 | 2.3 |
| L-1 | 0.0 | 0.2 | L-1 | 4.5 | 4.5 | L-1 | 0.8 | 4.5 | L-1 | 3.5 | 4.2 |
| L-3 | 3.5 | 3.5 | L-3 | 2.2 | 5.5 | L-3 | 3.3 | 5.5 | L-3 | 3.0 | 7.2 |
| L-5 | 11.0 | 10.2 | L-5 | 5.8 | 7.0 | L-5 | 3.0 | 4.0 | L-5 | 6.3 | 6.5 |

TABLE VI-continued

| | Without Lift | | | With 3 mm Lift | | | With 5 mm Lift | | | With 6 mm Lift | |
|---|---|---|---|---|---|---|---|---|---|---|---|
| | L | R | | L | R | | L | R | | L | R |
| S-1 | 5.0 | 3.5 | S-1 | 4.5 | 7.0 | S-1 | 7.5 | 6.0 | S-1 | 8.0 | 7.5 |

A 36-year-old male suffering from low back pain presented. Standing paraspinal EMG scans were performed without a lift, and with an 11 mm lift indicated by radiographic examination. The results are found in Table VII.

TABLE VII

| | Without Lift | With 11 mm Lift | |
|---|---|---|---|
| | L | L | R |
| T-1 | 0.7 0.9 | 4.5 | 2.9 |
| T-3 | 3.0 1.3 | 0.9 | 0.9 |
| T-5 | 3.0 2.8 | 1.0 | 1.0 |
| T-7 | 1.5 1.7 | 1.4 | 1.7 |
| T-9 | 2.2 2.8 | 2.2 | 3.1 |
| T-11 | 2.2 4.3 | 2.2 | 3.5 |
| L-1 | 2.1 4.5 | 2.5 | 3.3 |
| L-3 | 3.1 4.6 | 3.1 | 3.3 |
| L-5 | 3.5 5.0 | 4.6 | 4.5 |
| S-1 | 3.1 4.1 | 4.0 | 4.6 |

Discussion

By performing standing EMG scans, it is possible to determine if a favorable response to lift therapy occurred. In the first case, the 5 mm lift suggested by radiographic examination demonstrated the most favorable response. Although amplitudes increased at some levels, pattern symmetry was improved.

In the second case, the high reading at T-1 with the lift was due to patient fatigue and resulting difficulty remaining still. Of clinical interest, however, are the favorable changes in amplitude and symmetry at the T-3 and T-5 levels, and throughout the lumbar region.

EXAMPLE 20

The following is a case study using the method of this invention for EMG range of motion ("ROM") orthopedic exams:

Mrs. GE was a 47-year-old Hispanic woman complaining of low back pain and right knee pain that was unrelenting. Chiropractic care provided some relief, and she was required a 12 mm right shoe lift.

NEUTRAL

The following findings were obtained in the neutral position ROM EMG exam:

| | Neutral | | | |
|---|---|---|---|---|
| | | | Difference | |
| | L* | R* | L | R |
| T-1 | 64 | 44 | 20 | |
| T-3 | 56 | 56 | — | — |
| T-5 | 53 | 63 | | 10 |
| T-7 | 38 | 46 | | 8 |
| T-9 | 46 | 38 | 8 | |
| T-11 | 29 | 45 | | 16 |
| L-1 | 29 | 76 | | 47 |
| L3 | 28 | 45 | | 17 |
| L-5 | 35 | 43 | | 8 |
| S-1 | 41 | 43 | | 2 |

*millivolts

NEUTRAL

While there are generally low values associated with this chart, note that there are significant differences between the right and left side of T-1 and L-1. Most of the high readings in the neutral exam are on the right side, with a break at T-11 (R) to T-9 (L) and back to T-7 (R) while the general right sidedness of this chart was not a great problem.

The break between T-11 and T-7 warrants attention because of possible vertebral rotation with shearing and nerve root compression. The T-1 areas warrant further consideration that we will see in the flexion reading.

FLEXION

The flexion view in the following chart presents an entirely different situation:

| | FLEXION | | | |
|---|---|---|---|---|
| | | | Difference | |
| | L* | R* | L | R |
| T-1 | 44 | 83 | | 39 |
| T-3 | 135 | 80 | 55 | |
| T-5 | 75 | 77 | | 2 |
| T-7 | 59 | 77 | | 18 |
| T-9 | 64 | 66 | | 2 |
| T-11 | 67 | 79 | | 12 |
| L-1 | 169 | 92 | 77 | |
| L-3 | 54 | 67 | | 13 |
| L-5 | 74 | 66 | 8 | |
| S-1 | 57 | 65 | | 8 |

*millivolts

Here we find considerably higher values. Note that the transitional area of T-3 in the neutral is now represented by a dramatic change. T-5 slips from a moderate 2 (R) to a very active muscular swing to T-3 (L) and a strong pull back again to %-1 (R). The spine maintains its right sidedness from T-5 to T-011 and then makes a radical sweep from T-11 (R) to L-1 (L), back to L-5 (L) and once again to S-1 (R).

The patient told the operator she was experiencing "a lot of low back pain and can't hold this position long."

RIGHT LATERAL FLEXION

Compare the following right lateral flexion chart with the normal lateral flexion chart:

| | RIGHT LATERAL FLEXION | | | |
|---|---|---|---|---|
| | | | Difference | |
| | L* | R* | L | R |
| T-1 | 113 | 62 | 51 | |
| T-3 | 184 | 35 | 149 | |
| T-5 | 94 | 30 | 64 | |
| T-7 | 44 | 35 | 9 | |
| T-9 | 51 | 22 | 29 | |
| T-11 | 40 | 30 | 10 | |
| L-1 | 55 | 21 | 34 | |
| L-3 | 58 | 32 | 26 | |
| L-5 | 68 | 59 | 9 | |
| S-1 | 62 | 46 | 16 | |

*millivolts

This chart probably expresses this patient's most normal ROM. She experiences no pain, is comfortable, and can perform the test easily. Normal right flexion should exhibit a high left pattern. The areas of T-1 to T-5 persist in showing abnormally high readings apexing at T-3.

LEFT LATERAL FLEXION

As normal as right flexion was, left flexion exercise as shown in the following chart, shows general pathological asymmetry.

| LEFT LATERAL FLEXION | | | |
|---|---|---|---|
| | | Difference | |
| L* | R* | L | R |
| T-1 | 33 | 65 | | 32 |
| T-3 | 190 | 48 | 142 | |
| T-5 | 204 | 45 | 159 | |
| T-7 | 71 | 67 | 4 | |
| T-9 | 54 | 58 | | 4 |
| T-11 | 30 | 45 | | 15 |
| L-1 | 24 | 44 | | 20 |
| L-3 | 28 | 34 | | 6 |
| L-5 | 29 | 38 | | 9 |
| S-1 | 74 | 50 | 24 | |

*millivolts

Once again the normal patient pattern is broken with high readings at T-3 and T-5 (L). T-7 is moderately high with a reading of 71 (L) and 67 (R). The left flexion of this patient is almost entirely supported by the lower thoracic and lumbosacral muscles, the upper back muscles failing in providing support. In fact, these structures are acting antagonistically, forcing the lumbar structures to sustain excessive loading. This results in shearing at L-5/S-1 with concomitant disc stress and degenerative change.

RIGHT AND LEFT ROTATION

The following are the patients' normal right and left rotation charts:

| | L* | R* | Difference L | Difference R |
|---|---|---|---|---|
| RIGHT ROTATION | | | | |
| T-1 | 63 | 134 | | 71 |
| T-3 | 32 | 24 | 8 | |
| T-5 | 29 | 40 | | 11 |
| T-7 | 25 | 39 | | 14 |
| T-9 | 30 | 34 | | 4 |
| T-11 | 38 | 48 | | 10 |
| L-1 | 40 | 38 | 2 | |
| L-3 | 34 | 58 | | 24 |
| L-5 | 94 | 34 | 60 | |
| S-1 | 61 | 49 | 12 | |
| LEFT ROTATION | | | | |
| T-1 | 127 | 34 | 93 | |
| T-3 | 282 | 62 | 220 | |
| T-5 | 80 | 42 | 38 | |
| T-7 | 48 | 32 | 16 | |
| T-9 | 48 | 27 | 31 | |
| T-11 | 59 | 33 | 26 | |
| L-1 | 42 | 52 | | 10 |
| L-3 | 45 | 69 | | 24 |
| L-5 | 70 | 57 | 13 | |
| S-1 | 53 | 59 | | 6 |

*millivolts

These normal right and left rotation charts show a break at T-9 and T-11 with the high reading at the top of the side of rotation—that is, high right on right rotation and high left during left rotation.

This patient's chart again demonstrates the break of T-3 to the opposite side of the chart. L-3 again demonstrates aberrant readings with a strong right rotation. L-5 exhibits a very high reading of 94 (L) and 34 (R), a 300% counter rotation.

While left rotation demonstrates a greater tendency toward normalcy than right, this pattern also shows a downward shift of the normal crossover which should occur at T-10. In this patient, it occurs at T-12, forcing L-1/S-1 into a double switchback.

DISCUSSION

This EMG study is wholly consistent with x-ray and physical examination findings. During the patient's initial exam, she complained of pain between her shoulders, knee pain, and low back pain. The EMG indicated continuous T-3/T-5 and L-3/S-1 counter rotation and hypermobility during ROM studies. The whole six point exam is internally cohesive and self-reaffirming.

With this patient, the doctor should carefully consider deep tissue work to break muscle spasms at T-3, L-3/L-5. The pelvis should be stabilized with shoe lifts and orthotics. Proper biomechanical exercises are appropriate. Adjustive care to normalize the structural and functional dynamics of the spine is paramount.

The patient should be informed that most of her actions should be toward the right during times of stress, as right flexion is her most normal movement. A CT scan should be performed to evaluate the L-3 through S-1 intervertebral discs. The patient has experienced 50% relief under chiropractic care. This has enabled her to return to light duty as a file clerk.

What is claimed is:

1. A method of electromyographic scanning of paravertabral muscles comprising:
   measuring electrical potential with surface electrodes bilaterally across a first segment of a person'spinous process;
   progressing along the spinous process to a second segment of the spinous process; and
   measuring electrical potential with surface electrodes bilaterally across the second segment of the spinous process.

2. The method of claim 1 wherein every other spinal segment is measured bilaterally.

3. The method of claim 2 wherein said step of measuring is measured at the limit of a person's range of motion.

4. A method of determining paravertabral muscular hyperactivity in a person comprising:
   measuring electrical potential with surface electrodes bilaterally across a first segment of a person's spinous process to obtain an electrical potential measurement;
   progressing along the spinous process to a second segment of the spinous process;
   measuring electric potential with surface electrodes bilaterally across the second segment of the spinous process; and
   comparing the measurements to a predetermined scale of electrical potential measurements.

5. The method of claim 4 wherein every other spinal segment is measured bilaterally.

6. The method of claim 5 wherein said step of measuring is measured at the limit of a person's range of motion.

7. A method of electromyographic scanning of paravertabral muscles of the thoracic and lumbar spine comprising:

measuring electrical potential across a person's spinous process bilaterally at a first sacral level, fifth lumbar and every other segment of the spinous progress progressing cephalad and ending at the first thoracic segment.

8. The method of claim 7 wherein said electric potential is measured using surface electrodes.

9. The method of claim 8 wherein said step of measuring is measured at the limit of a person's range of motion.

10. A method of electromyographic scanning of paravertabral muscles of the thoracic and lumbar spine of a person comprising:

measuring electrical potential across the person's spinous process bilaterally at the first thoracic segment, at the third thoracic segment, and every other segment of the spinous process progressing caudad and ending at the first sacral level.

11. The method of claim 10 wherein said electric potential is measured using surface electrodes.

12. The method of claim 11 wherein said step of measuring is measured at the limit of a person's range of motion.

13. A method of determining areas of muscular hyperactivity in a prone person comprising:

electromyographic scanning comprising measuring electric potential with a surface electrode bilaterally across a first segment of a person's spinous process;

progressing along the spinous process to a second segment of the spinous process; and measuring the electric potential with surface electrodes bilaterally across the second segment to obtain electrical potential measurements with:
  (a) 0.3–0.5 uv readings indicating that muscles are in a resting state, and not actively contracting;
  (b) 0.6–0.7 uv readings indicating that some random firing above which may develop into problem areas;
  (c) 0.8–1.1 uv readings indicating problem areas exhibiting palpable spasticity and tenderness; and
  (d) 1.2 uv or greater readings indicating problem areas demonstrating pain and marked spasm.

14. The method of claim 13 wherein every other spinal segment is measured bilaterally.

15. The method of claim 14 wherein said step of measuring is measured at the limit of a person's range of motion.

* * * * *